Figure 1:
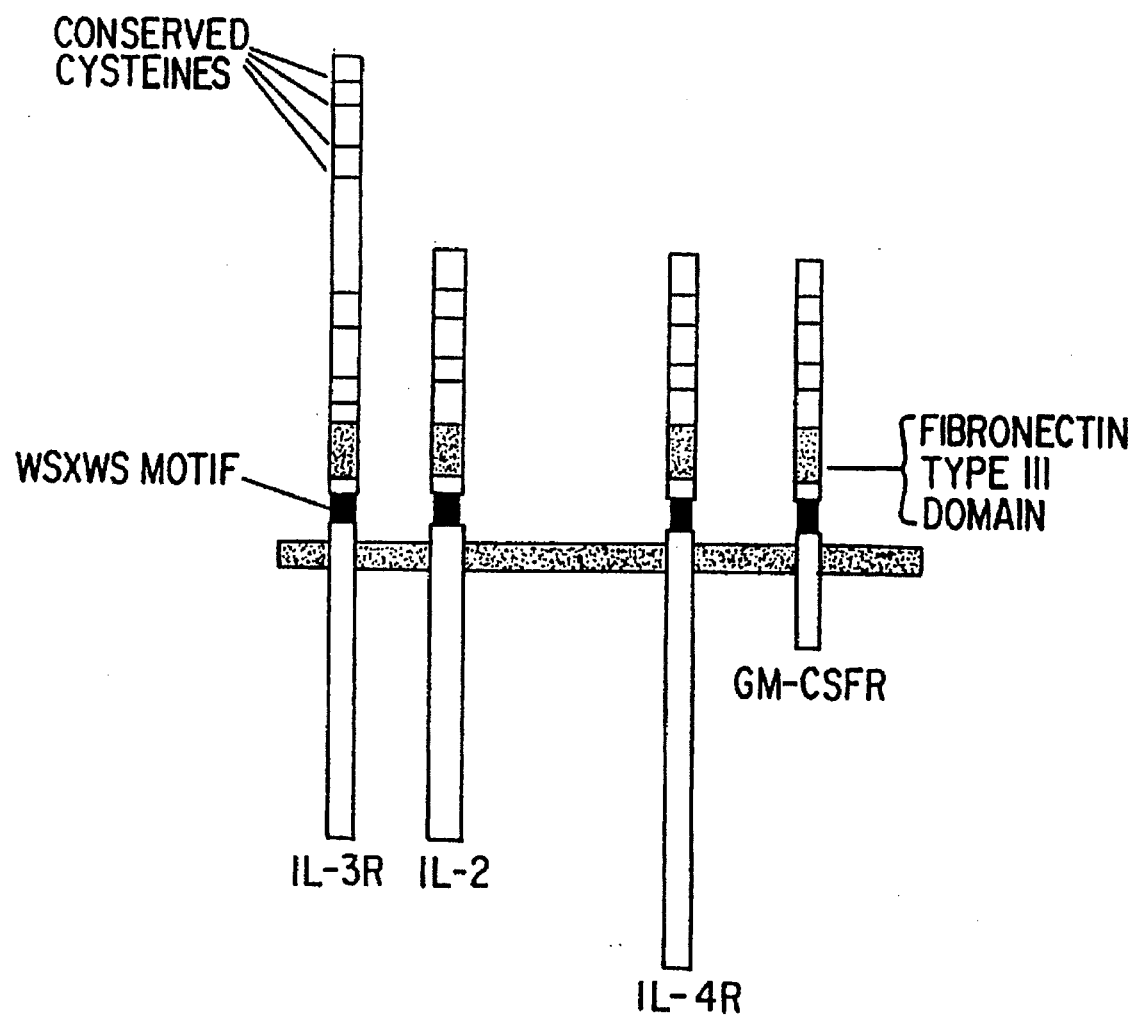

United States Patent

Snodgrass et al.

[11] Patent Number: 5,643,748
[45] Date of Patent: Jul. 1, 1997

[54] HU-B1.219, A NOVEL HUMAN HEMATOPOIETIN RECEPTOR

[75] Inventors: H. Ralph Snodgrass, Powell; Joseph Cioffi, Athens; Thomas Joel Zupancic, Worthington; Alan Wayne Shafer, Albany, all of Ohio

[73] Assignee: Progenitor, Inc., Columbus, Ohio

[21] Appl. No.: 306,231

[22] Filed: Sep. 14, 1994

[51] Int. Cl.⁶ .................. C07K 14/705; C12N 5/10; C12N 15/17

[52] U.S. Cl. .................. 435/69.1; 435/69.7; 435/252.3; 435/320.1; 530/350; 536/23.4; 536/23.5

[58] Field of Search .................. 435/69.1, 69.7, 435/252.3, 320.1; 530/350; 536/23.4, 23.5

Primary Examiner—John Ulm
Attorney, Agent, or Firm—Pennie & Edmonds

[57] ABSTRACT

The present invention relates to a novel member of the hematopoietin receptor family, herein referred to as Hu-B1.219. In particular, the invention relates to nucleotide sequences and expression vectors encoding Hu-B1.219 gene product. Genetically engineered host cells that express the Hu-B1.219 coding sequence may be used to evaluate and screen for ligands or drugs involved in Hu-B1.219 interaction and regulation. Since Hu-B1.219 expression has been detected in certain human fetal tissues and cancer cells, molecular probes designed from its nucleotide sequence may be useful for prenatal testing and cancer diagnosis.

14 Claims, 7 Drawing Sheets

```
           9           18          27          36          45          54
5' ACA GTA AAT TCT TTA GTT TTT CAA CCA ATA GAT GCA AAC TGG AAC ATA CAG TGC
   --- --- --- --- --- --- --- --- --- --- --- --- --- --- --- --- --- ---
    T   V   N   S   L   V   F   Q   P   I   D   A   N   W   N   I   Q   C 63          72          81          90          99         108
   TGG CTA AAA GGA GAC TTA AAA TTA TTC ATC TGT TAT GTG GAG TCA TTA TTT AAG
   --- --- --- --- --- --- --- --- --- --- --- --- --- --- --- --- --- ---
    W   L   K   G   D   L   K   L   F   I   C   Y   V   E   S   L   F   K 117         126         135         144         153         162
   AAT CTA GTC AGG AAT TAT AAC TAT AAG GTC CAT CTT TTA TAT GTT CTG CCT GAA
   --- --- --- --- --- --- --- --- --- --- --- --- --- --- --- --- --- ---
    N   L   V   R   N   Y   N   Y   K   V   H   L   L   Y   V   L   P   E 171         180         189         198         207         216
   GTG TTA GAA GAT TCA CCT CTG GTT CCC CAA AAA GGC AGT TTT CAG ATG GTT CAC
   --- --- --- --- --- --- --- --- --- --- --- --- --- --- --- --- --- ---
    V   L   E   D   S   P   L   V   P   Q   K   G   S   F   Q   M   V   H 225         234         243         252         261         270
   TGC AAT TGC AGT GTT CAT GAA TGT TGT GAA TGT CTT GTG CCT GTG CCA ACA GCC
   --- --- --- --- --- --- --- --- --- --- --- --- --- --- --- --- --- ---
    C   N   C   S   V   H   E   C   C   E   C   L   V   P   V   P   T   A 279         288         297         306         315         324
   AAA CTC AAC GAC ACT CTC CTT ATG TGT TTG AAA ATC ACA TCT GGT GGA GTA ATT
   --- --- --- --- --- --- --- --- --- --- --- --- --- --- --- --- --- ---
    K   L   N   D   T   L   L   M   C   L   K   I   T   S   G   G   V   I 333         342         351         360         369         378
   TTC CGG TCA CCT CTA ATG TCA GTT CAG CCC ATA AAT ATG GTG AAG CCT GAT CCA
   --- --- --- --- --- --- --- --- --- --- --- --- --- --- --- --- --- ---
    F   R   S   P   L   M   S   V   Q   P   I   N   M   V   K   P   D   P 387         396         405         414         423         432
   CCA TTA GGT TTG CAT ATG GAA ATC ACA GAT GAT GGT AAT TTA AAG ATT TCT TGG
   --- --- --- --- --- --- --- --- --- --- --- --- --- --- --- --- --- ---
    P   L   G   L   H   M   E   I   T   D   D   G   N   L   K   I   S   W 441         450         459         468         477         486
   TCC AGC CCA CCA TTG GTA CCA TTT CCA CTT CAA TAT CAA GTG AAA TAT TCA GAG
   --- --- --- --- --- --- --- --- --- --- --- --- --- --- --- --- --- ---
    S   S   P   P   L   V   P   F   P   L   Q   Y   Q   V   K   Y   S   E
```

FIG.2A

```
          495             504             513             522             531             540
AAT TCT ACA ACA GTT ATC AGA GAA GCT GAC AAG ATT GTC TCA GCT ACA TCC CTG
---  ---  ---  ---  ---  ---  ---  ---  ---  ---  ---  ---  ---  ---  ---  ---  ---  ---
 N   S   T   T   V   I   R   E   A   D   K   I   V   S   A   T   S   L 549             558             567             576             585             594
CTA GTA GAC AGT ATA CTT CCT GGG TCT TCG TAT GAG GTT CAG GTG AGG GGC AAG
---  ---  ---  ---  ---  ---  ---  ---  ---  ---  ---  ---  ---  ---  ---  ---  ---  ---
 L   V   D   S   I   L   P   G   S   S   Y   E   V   Q   V   R   G   K 603             612             621             630             639             648
AGA CTG GAT GGC CCA GGA ATC TGG AGT GAC TGG AGT ACT CCT CGT GTC TTT ACC
---  ---  ---  ---  ---  ---  ---  ---  ---  ---  ---  ---  ---  ---  ---  ---  ---  ---
 R   L   D   G   P   G   I   W   S   D   W   S   T   P   R   V   F   T 657             666             675             684             693             702
ACA CAA GAT GTC ATA TAC TTT CCA CCT AAA ATT CTG ACA AGT GTT GGG TCT AAT
---  ---  ---  ---  ---  ---  ---  ---  ---  ---  ---  ---  ---  ---  ---  ---  ---  ---
 T   Q   D   V   I   Y   F   P   P   K   I   L   T   S   V   G   S   N 711             720             729             738             747             756
GTT TCT TTT CAC TGC ATC TAT AAG AAG GAA AAC AAG ATT GTT CCC TCA AAA GAG
---  ---  ---  ---  ---  ---  ---  ---  ---  ---  ---  ---  ---  ---  ---  ---  ---  ---
 V   S   F   H   C   I   Y   K   K   E   N   K   I   V   P   S   K   E 765             774             783             792             801             810
ATT GTT TGG TGG ATG AAT TTA GCT GAG AAA ATT CCT CAA AGC CAG TAT GAT GTT
---  ---  ---  ---  ---  ---  ---  ---  ---  ---  ---  ---  ---  ---  ---  ---  ---  ---
 I   V   W   W   M   N   L   A   E   K   I   P   Q   S   Q   Y   D   V 819             828             837             846             855             864
GTG AGT GAT CAT GTT AGC AAA GTT ACT TTT TTC AAT CTG AAT GAA ACC AAA CCT
---  ---  ---  ---  ---  ---  ---  ---  ---  ---  ---  ---  ---  ---  ---  ---  ---  ---
 V   S   D   H   V   S   K   V   T   F   F   N   L   N   E   T   K   P 873             882             891             900             909             918
CGA GGA AAG TTT ACC TAT GAT GCA GTG TAC TGC TGC AAT GAA CAT GAA TGC CAT
---  ---  ---  ---  ---  ---  ---  ---  ---  ---  ---  ---  ---  ---  ---  ---  ---  ---
 R   G   K   F   T   Y   D   A   V   Y   C   C   N   E   H   E   C   H 927             936             945             954             963             972
CAT CGC TAT GCT GAA TTA TAT GTG ATT GAT GTC AAT ATC AAT ATC TCA TGT GAA
---  ---  ---  ---  ---  ---  ---  ---  ---  ---  ---  ---  ---  ---  ---  ---  ---  ---
 H   R   Y   A   E   L   Y   V   I   D   V   N   I   N   I   S   C   E
```

FIG.2B

```
      981         990         999        1008        1017        1026
ACT GAT GGG TAC TTA ACT AAA ATG ACT TGC AGA TGG TCA ACC AGT ACA ATC CAG
--- --- --- --- --- --- --- --- --- --- --- --- --- --- --- --- --- ---
 T   D   G   Y   L   T   K   M   T   C   R   W   S   T   S   T   I   Q 1035        1044        1053        1062        1071        1080
TCA CTT GCG GAA AGC ACT TTG CAA TTG AGG TAT CAT AGG AGC AGC CTT TAC TGT
--- --- --- --- --- --- --- --- --- --- --- --- --- --- --- --- --- ---
 S   L   A   E   S   T   L   Q   L   R   Y   H   R   S   S   L   Y   C 1089        1098        1107        1116        1125        1134
TCT GAT ATT CCA TCT ATT CAT CCC ATA TCT GAG CCC AAA GAT TGC TAT TTG CAG
--- --- --- --- --- --- --- --- --- --- --- --- --- --- --- --- --- ---
 S   D   I   P   S   I   H   P   I   S   E   P   K   D   C   Y   L   Q 1143        1152        1161        1170        1179        1188
AGT GAT GGT TTT TAT GAA TGC ATT TTC CAG CCA ATC TTC CTA TTA TCT GGC TAC
--- --- --- --- --- --- --- --- --- --- --- --- --- --- --- --- --- ---
 S   D   G   F   Y   E   C   I   F   Q   P   I   F   L   L   S   G   Y 1197        1206        1215        1224        1233        1242
ACA ATG TGG ATT AGG ATC AAT CAC TCT CTA GGT TCA CTT GAC TCT CCA CCA ACA
--- --- --- --- --- --- --- --- --- --- --- --- --- --- --- --- --- ---
 T   M   W   I   R   I   N   H   S   L   G   S   L   D   S   P   P   T 1251        1260        1269        1278        1287        1296
TGT GTC CTT CCT GAT TCT GTG GTG AAG CCA CTG CCT CCA TCC AGT GTG AAA GCA
--- --- --- --- --- --- --- --- --- --- --- --- --- --- --- --- --- ---
 C   V   L   P   D   S   V   V   K   P   L   P   P   S   S   V   K   A 1305        1314        1323        1332        1341        1350
GAA ATT ACT ATA AAC ATT GGA TTA TTG AAA ATA TCT TGG GAA AAG CCA GTC TTT
--- --- --- --- --- --- --- --- --- --- --- --- --- --- --- --- --- ---
 E   I   T   I   N   I   G   L   L   K   I   S   W   E   K   P   V   F 1359        1368        1377        1386        1395        1404
CCA GAG AAT AAC CTT CAA TTC CAG ATT CGC TAT GGT TTA AGT GGA AAA GAA GTA
--- --- --- --- --- --- --- --- --- --- --- --- --- --- --- --- --- ---
 P   E   N   N   L   Q   F   Q   I   R   Y   G   L   S   G   K   E   V 1413        1422        1431        1440        1449        1458
CAA TGG AAG ATG TAT GAG GTT TAT GAT GCA AAA TCA AAA TCT GTC AGT CTC CCA
--- --- --- --- --- --- --- --- --- --- --- --- --- --- --- --- --- ---
 Q   W   K   M   Y   E   V   Y   D   A   K   S   K   S   V   S   L   P
```

FIG.2C

```
          1467        1476        1485        1494        1503        1512
GTT CCA GAC TTG TGT GCA GTC TAT GCT GTT CAG GTG CGC TGT AAG AGG CTA GAT
--- --- --- --- --- --- --- --- --- --- --- --- --- --- --- --- --- ---
 V   P   D   L   C   A   V   Y   A   V   Q   V   R   C   K   R   L   D 1521        1530        1539        1548        1557        1566
GGA CTG GGA TAT TGG AGT AAT TGG AGC AAT CCA GCC TAC ACA GTT GTC ATG GAT
--- --- --- --- --- --- --- --- --- --- --- --- --- --- --- --- --- ---
 G   L   G   Y   W   S   N   W   S   N   P   A   Y   T   V   V   M   D 1575        1584        1593        1602        1611        1620
ATA AAA GTT CCT ATG AGA GGA CCT GAA TTT TGG AGA ATA ATT AAT GGA GAT ACT
--- --- --- --- --- --- --- --- --- --- --- --- --- --- --- --- --- ---
 I   K   V   P   M   R   G   P   E   F   W   R   I   I   N   G   D   T 1629        1638        1647        1656        1665        1674
ATG AAA AAG GAG AAA AAT GTC ACT TTA CTT TGG AAG CCC CTG ATG AAA AAT GAC
--- --- --- --- --- --- --- --- --- --- --- --- --- --- --- --- --- ---
 M   K   K   E   K   N   V   T   L   L   W   K   P   L   M   K   N   D 1683        1692        1701
TCA TTG TGC AGT GTT CAG AGA TAT GTG ATA AAC 3'
--- --- --- --- --- --- --- --- --- --- ---
 S   L   C   S   V   Q   R   Y   V   I   N
```

FIG.2D

SPACING OF CONSERVED AMINO ACIDS IN THE EXTRACELLULAR DOMAINS OF KNOWN CYTOKINE RECEPTOR GENES

..C...C........C....C.............A/PP.L/V.....W.....Y..........L...Y..R...G.WSXWS..
(10-11) (28-35) (9-16) (36-48) (2-3) (13-18) (12-20) (26-33) (5-6)(5)(6-11)(2)

CONSERVED AMINO ACIDS IN THE 5' EXTRACELLULAR DOMAINS OF CLONE Hu-B1.219

..C...C..........C....C..............PP.L.......W.....Y..........L...Y..R...G.WSDWS..
(11) (44) (10) (43) (3) (14) (12) (30) (5) (5)(8)(2)

CONSERVED AMINO ACIDS IN THE 3' EXTRACELLULAR DOMAINS OF CLONE Hu-B1.219

..C...C..........C....C..............PP.V.......W.....Y..........P...Y..R...G.WSNWS..
(11) (41) (10) (41) (3) (15) (16) (27) (6) (5)(8)(2)

FIG.3

```
                        *  -  *  -  *  -
mIL2Rβ              E P Y L E F E A R R R L L
hIL2Rγ              E H L V Q Y R T D W D H S
mIL5Rα              D H C F N Y E L K I Y N T
mEPOR               T T H I R Y E V D V S A G
Hu-B1.219(5')       P F P L Q Y Q V K Y Q V K
Hu-B1.219(3')       Q F Q I R Y G L S G K E V

HYDROPHOBIC:    "*"
HYDROPHILIC:    "-"
```

FIG.4

```
                        * b * b * b
mIL-2Rβ             S T S Y E V Q V R V K A Q R N
hIL-2Rγ             Q K R Y T F R V R S R F N P L
mIL-5Rα             L S K Y D V Q V R A A V S S M
mEPOR               G T R Y T F A V R A R M A P S
Hu-B1.219(5')       G S S Y E V Q V R G K R L D G
Hu-B1.219(3')       C A V Y A V Q V R C K R L D G
                            Y       R

HYDROPHOBIC:    "*"
BASIC:          "b"
```

FIG.5

HU-B1.219, A NOVEL HUMAN HEMATOPOIETIN RECEPTOR

1. INTRODUCTION

The present invention relates to a novel member of the hematopoietin receptor family, herein referred to as Hu-B1.219. In particular, the invention relates to nucleotide sequences and expression vectors encoding Hu-B1.219 gene product. Genetically engineered host cells that express the Hu-B1.219 coding sequence may be used to evaluate and screen for ligands or drugs involved in Hu-B1.219 interaction and regulation. Since Hu-B1.219 expression has been detected in certain human fetal tissues and cancer cells, molecular probes designed from its nucleotide sequence may be useful for prenatal testing and cancer diagnosis.

2. BACKGROUND OF THE INVENTION

A variety of diseases, including malignancy and immunodeficiency, are related to malfunction within the lympho-hematopoietic system. Some of these conditions could be alleviated and/or cured by repopulating the hematopoietic system with progenitor cells, which when triggered to differentiate would overcome the patient's deficiency. Therefore, the ability to initiate and regulate hematopoiesis is of great importance (McCune et al., 1988, Science 241:1632).

The process of blood cell formation, by which a small number of self-renewing stem cells give rise to lineage specific progenitor cells that subsequently undergo proliferation and differentiation to produce the mature circulating blood cells has been shown to be at least in part regulated by specific hormones. These hormones are collectively known as hematopoietic growth factors or cytokines (Metcalf, 1985, Science 229:16; Dexter, 1987, J. Cell Sci. 88:1; Golde and Gasson, 1988, Scientific American, July:62; Tabbara and Robinson, 1991, Anti-Cancer Res. 11:81; Ogawa, 1989, Environ. Health Presp. 80:199; Dexter, 1989, Br. Med. Bull. 45:337).

With the advent of recombinant DNA technology, the genes encoding a number of these molecules have now been molecularly cloned and expressed in recombinant form (Souza et al., 1986, Science 232:61; Gough et al., 1984, Nature 309:763; Yokota et al., 1984, Proc. Natl. Acad. Sci. U.S.A. 81:1070; Kawasaki et al., 1985, Science 230:291). These cytokines have been studied in their structure, biology and even therapeutic potential. Some of the most well characterized factors include erythropoietin (EPO), stem cell factor (SCF), granulocyte macrophage colony stimulating factor (GM-CSF), macrophage colony stimulating factor (M-CSF), granulocyte colony stimulating factor (G-CSF), and the interleukins (IL-1 to IL-14).

These factors act on different cell types at different stages during blood cell development, and their potential uses in medicine are far-reaching which include blood transfusions, bone marrow transplantation, correcting immunosuppressive disorders, cancer therapy, wound healing, and activation of the immune response. (Golde and Gasson, 1988, Scientific American, July:62).

Apart from inducing proliferation and differentiation of hematopoietic progenitor cells, such cytokines have also been shown to activate a number of functions of mature blood cells (Stanley et al., 1976, J. Exp. Med. 143:631; Schrader et al., 1981, Proc. Natl. Acad. Sci. U.S.A. 78:323; Moore et al., 1980, J. Immunol. 125:1302; Kurland et al., 1979, Proc. Natl. Acad. Sci. U.S.A. 76:2326; Handman and Burgess, 1979, J. Immunol. 122:1134; Vadas et al., 1983, Blood 61:1232; Vadas et al., 1983, J. Immunol. 130:795), including influencing the migration of mature hematopoietic cells (Weibart et al., 1986, J. Immunol. 137:3584).

Cytokines exert their effects on target cells by binding to specific cell surface receptors. A number of cytokine receptors have been identified and the genes encoding them molecularly cloned. Several cytokine receptors have recently been classified into a hematopoietin receptor (HR) superfamily. The grouping of these receptors was based on the conservation of key amino acid motifs in the extracellular domains (Bazan, 1990, Immunology Today 11:350) (FIG. 1). The HR family is defined by three conserved motifs in the extracellular domain of these receptors. The first is a Trp-Ser-X-Trp-Ser (WSXWS box) motif (SEQ ID NO:1) which is highly conserved and located amino-terminal to the transmembrane domain. Most members of the HR family contain this motif. The second consists of four conserved cysteine residues located in the N-terminal half of the extracellular region. The third is a conserved fibronectin Type III (FN III) domain which is located between the WSXWS box and the cysteines. The members of the HR family include receptors for ligands such as erythropoietin (EPO), granulocyte colony stimulating factor (G-CSF) (Fukunaga, 1990, Cell 61:341), granulocyte-macrophage colony stimulating factor (GM-CSF), interleukin-3 (IL-3), IL-4, IL-5, IL-6, IL-7, and IL-2 (β-subunit) (Cosman, 1990, TIBS 15:265).

Ligands for the HR are critically involved in the maturation and differentiation of blood cells. For example, IL-3 promotes the proliferation of early multilineage pluripotent stem cells, and synergizes with EPO to produce red cells. IL-6 and IL-3 synergize to induce proliferation of early hematopoietic precursors. GM-CSF has been shown to induce the proliferation of granulocytes as well as increase macrophage function. IL-7 is a bone marrow-derived cytokine that plays a role in producing immature T and B lymphocytes. IL-4 induces proliferation of antigen-primed B cells and antigen-specific T cells. Thus, members of this receptor superfamily are involved in the regulation of the hematopoietic system.

3. SUMMARY OF THE INVENTION

The present invention relates to a novel member of the HR family, referred to as Hu-B1.219. In particular, it relates to the nucleotide sequences, expression vectors, and host cells expressing the Hu-B1.219 gene.

The invention is based, in part, upon Applicants' discovery of a cDNA clone, Hu-B1.219, isolated from a human fetal liver cDNA library. While the nucleotide sequence of this clone shares certain homology with other HR genes, it is also unique in its structure. The human sequence is expressed in certain human fetal and tumor cells. Therefore, a wide variety of uses are encompassed by the present invention, including but not limited to, the diagnosis of cancer, the marking of fetal tissues, and the screening of ligands and compounds that bind the receptor molecule encoded by Hu-B1.219.

For the purpose of the present invention, the designation Hu-B1.219 refers to the partial cDNA sequence disclosed in FIGS. 2A–2D. In addition, Hu-B1.219 also refers to the entire coding sequence of which the cDNA sequence of FIGS. 2A–2D is a part.

4. BRIEF DESCRIPTION OF THE DRAWINGS

FIG. 1. A schematic drawing of conserved regions shared by members of HR family.

FIGS. 2A–2D. Nucleotide sequence (SEQ ID NO:2) and deduced amino acid sequence (SEQ ID NO:3) of Hu-B1.219.

FIG. 3. Comparison of the spacing of conserved amino acids in the FN III domain between HR genes and Hu-B1.219.

FIG. 4. Comparison of conserved motifs between HR molecules and Hu-B1.219 in "Block 3" mIL2Rβ (SEQ ID NO:4); hIL2R$_γ$ (SEQ ID NO:5); mIL5Rα (SEQ ID NO: 6); mEPOR (SEQ ID NO:7); Hu-B1.219(5') (SEQ ID NO:8); Hu-B1.219(3') (SEQ ID NO:9).

FIG. 5. Comparison of conserved motifs between HR molecules and Hu-B1.219 in "Block 6" mIL-2Rβ (SEQ ID NO:10); hIL-2R$_γ$ (SEQ ID NO:11); mIL-5Rα (SEQ ID NO:12); mEPOR (SEQ ID NO:13); Hu-B1.219(5') (SEQ ID NO:14); Hu-B1.219(3') (SEQ ID NO:15).

5. DETAILED DESCRIPTION OF THE INVENTION

5.1 THE Hu-B1.219 CODING SEQUENCE

The present invention relates to nucleic acid and amino acid sequences of a novel member of the HR family. In a specific embodiment by way of example in Section 6, infra, a new member of this HR family of receptors was cloned and characterized. The nucleotide coding sequence and deduced amino acid sequence of the novel receptor are unique, and the receptor is referred to as Hu-B1.219. In accordance with the invention,. any nucleotide sequence which encodes the amino acid sequence of the Hu-B1.219 gene product can be used to generate recombinant molecules which direct the expression of Hu-B1.219 gene.

Analysis of the Hu-B1.219 sequence revealed significant homology to the FN III domain of the HR family indicating that it was a member of the HR family of receptors. The shared homology between Hu-B1.219 and other known members of the HR family is discussed in Section 6.2, infra. However, this receptor also contains regions of previously unreported unique nucleotide sequences.

Northern blot hybridization analysis, indicates that Hu-B1.219 mRNA is highly expressed in cells of hematopoietic origin. In addition, the Hu-B1.219 sequence is expressed in certain tumor cells.

In order to clone the full length cDNA sequence encoding the entire Hu-B1.219 cDNA, labeled DNA probes made from nucleic acid fragments corresponding to any portion of the partial cDNA disclosed herein may be used to screen the human fetal liver cDNA library. More specifically, oligonucleotides corresponding to either the 5' or 3' terminus of the partial cDNA sequence may be used to obtain longer nucleotide sequences. Briefly, the library will be plated out to yield a maximum of 30,000 pfu for each 150 mm plate. Approximately 40 plates may be screened. The plates are incubated at 37° C. until the plaques reach a diameter of 0.25 mm or are just beginning to make contact with one another (3–8 hours). Nylon filters are placed onto the soft top agarose and after 60 seconds, the filters are peeled off and floated on a DNA denaturing solution consisting of 0.4N sodium hydroxide. The filters are then immersed in neutralizing solution consisting of 1M Tris HCL, pH 7.5, before being allowed to air dry. The filters are prehybridized in casein hybridization buffer containing 10% dextran sulfate, 0.5M NaCl, 50mM Tris HCL, pH 7.5, 0.1% sodium pyrophosphate, 1% casein, 1% SDS, and denatured salmon sperm DNA at 0.5 mg/ml for 6 hours at 60° C. The radiolabeled probe is then denatured by heating to 95° C. for 2 minutes and then added to the prehybridization solution containing the filters. The filters are hybridized at 60° C. for 16 hours. The filters are then washed in 1×wash mix (10×wash mix contains 3M NaCl, 0.6M Tris base, and 0.02M EDTA) twice for 5 minutes each at room temperature, then in 1×wash mix containing 1% SDS at 60° C. for 30 minutes, and finally in 0.3×wash mix containing 0.1% SDS at 60° C. for 30 minutes. The filters are then air dried and exposed to x-ray film for autoradiography. After developing, the film is aligned with the filters to select a positive plaque. If a single, isolated positive plaque cannot be obtained, the agar plug containing the plaques will be removed and placed in lambda dilution buffer containing 0.1M NaCl, 0.01M magnesium sulfate, 0.035M Tris HCl, pH 7.5, 0.01% gelatin. The phage will then be replated and rescreened to obtain single, well isolated positive plaques. Positive plaques may be isolated and the cDNA clones sequenced using primers based on the known cDNA sequence. This step may be repeated until a full length cDNA is obtained.

It may be necessary to screen multiple cDNA libraries from different tissues to obtain a full length cDNA. In the event that it is difficult to identify cDNA clones encoding the complete 5' terminal coding region, an often encountered situation in cDNA cloning, the RACE (Rapid Amplification of cDNA Ends) technique may be used. RACE is a proven PCR-based strategy for amplifying the 5' end of incomplete cDNAs. 5'-RACE-Ready cDNA synthesized from human fetal liver containing a unique anchor sequence is commercially available (Clontech). To obtain the 5' end of the cDNA, PCR is carried out on 5'-RACE-Ready cDNA using the provided anchor primer and the 3' primer. A secondary PCR reaction is then carried out using the anchored primer and a nested 3' primer according to the manufacturer's instructions. Once obtained, the full length cDNA sequence may be translated into amino acid sequence and examined for certain landmarks such as a continuous open reading frame flanked by translation initiation and termination sites, a potential signal sequence and transmembrane domain, and finally overall structural similarity to known HR genes.

5 5.2 EXPRESSION OF Hu-B1.219 SEQUENCE

In accordance with the invention, Hu-B1.219 polynucleotide sequence which encodes the Hu-B1.219 protein, peptide fragments of Hu-B1.219, Hu-B1.219 fusion proteins or functional equivalents thereof, may be used to generate recombinant DNA molecules that direct the expression of Hu-B1.219 protein, Hu-B1.219 peptide fragment, fusion proteins or a functional equivalent thereof, in appropriate host cells. Such Hu-B1.219 polynucleotide sequences, as well as other polynucleotides which selectively hybridize to at least a part of such Hu-B1.219 polynucleotides or their complements, may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the Hu-B1.219 protein. Such DNA sequences include those which are capable of hybridizing to the human Hu-B1.219 sequences under stringent conditions. The phrase "stringent conditions" as used herein refers to those hybridizing conditions that (1) employ low ionic strength and high temperature for washing, for example, 0.015M NaCl/0.0015M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75M NaCl, 0.075M Sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within a Hu-B1.219 sequence, which result in a silent change thus producing a functionally equivalent Hu-B1.219 protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequences of the invention may be engineered in order to alter an Hu-B1.219 coding sequence for a variety of ends including but not limited to alterations which modify processing and expression of the gene product. For example, mutations may be introduced using techniques which are well known in the art, e.g., site-directed mutagenesis, to insert new restriction sites, to alter glycosylation patterns, phosphorylation, etc.

In another embodiment of the invention, an Hu-B1.219 or a modified Hu-B1.219 sequence may be ligated to a heterologous sequence to encode a fusion protein. For example, for screening of peptide libraries for inhibitors or stimulators of Hu-B1.219 activity, it may be useful to encode a chimeric Hu-B1.219 protein expressing a heterologous epitope that is recognized by a commercially available antibody. A fusion protein may also be engineered to contain a cleavage site located between a Hu-B1.219 sequence and the heterologous protein sequence, so that the Hu-B1.219 may be cleaved away from the heterologous moiety.

In an alternate embodiment of the invention, the coding sequence of a Hu-B1.219 could be synthesized in whole or in part, using chemical methods well known in the art. See, for example, Caruthers et al., 1980, *Nuc. Acids Res. Symp. Ser.* 7:215–233; Crea and Horn, 180, *Nuc. Acids Res.* 9(10):2331; Matteucci and Caruthers, 1980, *Tetrahedron Letters* 21:719; and Chow and Kempe, 1981, *Nuc. Acids Res.* 9(12):2807–2817. Alternatively, the protein itself could be produced using chemical methods to synthesize an Hu-B1.219 amino acid sequence in whole or in part. For example, peptides can be synthesized by solid phase techniques, cleaved from the resin, and purified by preparative high performance liquid chromatography. (e.g., see Creighton, 1983, *Proteins Structures And Molecular Principles*, W. H. Freeman and Co., N.Y. pp. 50–60). The composition of the synthetic peptides may be confirmed by amino acid analysis or sequencing (e.g., the Edman degradation procedure; see Creighton, 1983, *Proteins, Structures and Molecular Principles*, W. H. Freeman and Co., N.Y., pp. 34–49).

In order to express a biologically active Hu-B1.219, the nucleotide sequence coding for Hu-B1.219, or a functional equivalent, is inserted into an appropriate expression vector, i.e., a vector which contains the necessary elements for the transcription and translation of the inserted coding sequence. The Hu-B1.219 gene products as well as host cells or cell lines transfected or transformed with recombinant Hu-B1.219 expression vectors can be used for a variety of purposes. These include but are not limited to generating antibodies (i.e., monoclonal or polyclonal) that competitively inhibit activity of an Hu-B1.219 and neutralize its activity; and antibodies that mimic the activity of Hu-B1.219 ligands in stimulating the receptor to transmit an intracellular signal. Anti-Hu-B1.219 antibodies may be used in detecting and quantifying expression of Hu-B1.219 levels in cells and tissues.

5.3 EXPRESSION SYSTEMS

Methods which are well known to those skilled in the art can be used to construct expression vectors containing the Hu-B1.219 coding sequence and appropriate transcriptional/translational control signals. These methods include in vitro recombinant DNA techniques, synthetic techniques and in vivo recombination/genetic recombination. See, for example, the techniques described in Sambrook et al., 1989, Molecular Cloning A Laboratory Manual, Cold Spring Harbor Laboratory, New York and Ausubel et al., 1989, Current Protocols in Molecular Biology, Greene Publishing Associates and Wiley Interscience, New York.

A variety of host-expression vector systems may be utilized to express the Hu-B1.219 coding sequence. These include but are not limited to microorganisms such as bacteria transformed with recombinant bacteriophage DNA, plasmid DNA or cosmid DNA expression vectors containing the Hu-B1.219 coding sequence; yeast transformed with recombinant yeast expression vectors containing the Hu-B1.219 coding sequence; insect cell systems infected with recombinant virus expression vectors (e.g., baculovirus) containing the Hu-B1.219 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Hu-B1.219 coding sequence; or animal cell systems The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the Hu-B1.219 DNA, SV40-, BPV- and EBV-based vectors may be used with an appropriate selectable marker.

In bacterial systems a number of expression vectors may be advantageously selected depending upon the use intended for the Hu-B1.219 expressed. For example, when large quantities of Hu-B1.219 are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., 1983, EMBO J. 2:1791), in which the Hu-B1.219 coding sequence may be ligated into the vector in frame with the lac Z coding region so that a hybrid AS-lac Z protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, New York, Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the Hu-B1.219 coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9.

An alternative expression system which could be used to express Hu-B1.219 is an insect system. In one such system, *Autographa californica* nuclear polyhidrosis virus (AcNPV) is used as a vector to express foreign genes. The virus grows in *Spodoptera frugiperda* cells. The Hu-B1.219 coding sequence may be cloned into non-essential regions (for example the polyhedrin gene) of the virus and placed under control of an AcNPV promoter (for example the polyhedrin promoter). Successful insertion of the Hu-B1.219 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the Hu-B1.219 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing Hu-B1.219 in infected hosts. (e.g., See Logan & Shenk, 1984, Proc. Natl. Acad. Sci. U.S.A. 81:3655–3659). Alternatively, the vaccinia 7.5K promoter may be used. (See, e.g., Mackett et al., 1982, Proc. Natl. Acad. Sci. U.S.A. 79:7415–7419; Mackett et al., 1984, J. Virol. 49:857–864; Panicali et al., 1982, Proc. Natl. Acad. Sci. U.S.A. 79:4927–4931).

Specific initiation signals may also be required for efficient translation of inserted Hu-B1.219 coding sequences. These signals include the ATG initiation codon and adjacent sequences. In cases where the entire Hu-B1.219 gene, including its own initiation codon and adjacent sequences, is inserted into the appropriate expression vector, no additional translational control signals may be needed. However, in cases where only a portion of the Hu-B1.219 coding sequence is inserted, exogenous translational control signals, including the ATG initiation codon, must be provided. Furthermore, the initiation codon must be in phase with the reading frame of the Hu-B1.219 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. The presence of several consensus N-glycosylation sites in the Hu-B1.219 extracellular domain support the possibility that proper modification may be important for Hu-B1.219 function. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the Hu-B1.219 may be engineered. Rather than using expression vectors which contain viral origins of replication, host cells can be transformed with the Hu-B1.219 DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Hu-B1.219 on the cell surface. Such engineered cell lines are particularly useful in screening for ligands or drugs that affect Hu-B1.219 function.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. U.S.A. 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for dhfr, which confers resistance to methotrexate (Wigler, et al., 1980, Natl. Acad. Sci. U.S.A. 77:3567; O'Hare, et al., 1981, Proc. Natl. Acad. Sci. U.S.A. 78:1527); gpt, which confers resistance to mycophenolic acid (Mulligan & Berg, 1981), Proc. Natl. Acad. Sci. U.S.A. 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. U.S.A. 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.4 IDENTIFICATION OF CELLS THAT EXPRESS Hu-B1.219

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of Hu-B1.219 mRNA transcripts in the host cell; and (d) detection of the gene product as measured by immunoassay or by its biological activity. Prior to the identification of gene expression, the host cells may be first mutagenized in an effort to increase the level of expression of Hu-B1.219, especially in cell lines that produce low amounts of Hu-B1.219.

In the first approach, the presence of the Hu-B1.219 coding sequence inserted in the expression vector can be detected by DNA-DNA or DNA-RNA hybridization using probes comprising nucleotide sequences that are homologous to the Hu-B1.219 coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the Hu-B1.219 coding sequence is inserted within a marker gene sequence of the vector, recombinants containing the Hu-B1.219 coding sequence can be identified by the absence of the marker gene function. Alternatively, a marker gene can be placed in tandem with the Hu-B1.219 sequence under the control of the same or different promoter used to control the expression of the Hu-B1.219 coding sequence. Expression of the marker in response to induction or selection indicates expression of the Hu-B1.219 coding sequence.

In the third approach, transcriptional activity for the Hu-B1.219 coding region can be assessed by hybridization assays. For example, RNA can be isolated and analyzed by Northern blot using a probe homologous to the Hu-B1.219 coding sequence or particular portions thereof. Alternatively, total nucleic acids of the host cell may be extracted and assayed for hybridization to such probes.

In the fourth approach, the expression of the Hu-B1.219 protein product can be assessed immunologically, for example by Western blots, immunoassays such as radioimmuno-precipitation, enzyme-linked immunoassays and the like.

5.5 USES OF Hu-B1.219 ENGINEERED CELL LINES

In an embodiment of the invention, the Hu-B1.219 receptor and/or cell lines that express the Hu-B1.219 receptor may be used to screen for antibodies, peptides, or other ligands that act as agonists or antagonists of the Hu-B1.219 receptor. For example, anti-Hu-B1.219 antibodies may be used to inhibit or stimulate receptor Hu-B1.219 function. Alternatively, be screening of peptide libraries with recombinantly expressed soluble Hu-B1.219 protein or cell lines expressing Hu-B1.219 protein may be useful for identification of therapeutic molecules that function by inhibiting or stimulating the biological activity of Hu-B1.219. The uses of the Hu-B1.219 receptor and engineered cell lines, described in the subsections below, may be employed equally well for other members of the HR family.

In an embodiment of the invention, engineered cell lines which express most of the Hu-B1.219 coding region or its ligand binding domain or its ligand binding domain fused to another molecule such as the immunoglobulin constant region (Hallenbaugh and Aruffo, 1992, Current Protocols in Immunology, Unit 10.19; Aruffo et al., 1990, Cell 61:1303) may be utilized to produce a soluble receptor to screen and identify ligand antagonists as well as agonists. The soluble Hu-B1.219 protein or fusion protein may be used to identify a ligand in binding assays, affinity chromatography, immunoprecipitation, Western blot, and the like. Alternatively, the ligand binding domain of Hu-B1.219 may be fused to the coding sequence of the epidermal growth factor receptor transmembrane and cytoplasmic regions. This approach provides for the use of the epidermal growth factor receptor signal transduction pathway as a means for detecting ligands that bind to Hu-B1.219 in a manner capable of triggering an intracellular signal. Synthetic compounds, natural products, and other sources of potentially biologically active materials can be screened in a number of ways.

Random peptide libraries consisting of all possible combinations of amino acids attached to a solid phase support may be used to identify peptides that are able to bind to the ligand binding site of a given receptor or other functional domains of a receptor such as kinase domains (Lam, K. S. et al., 1991, Nature 354: 82–84). The screening of peptide libraries may have therapeutic value in the discovery of pharmaceutical agents that stimulate or inhibit the biological activity of receptors through their interactions with the given receptor.

Identification of molecules that are able to bind to the Hu-B1.219 may be accomplished by screening a peptide library with recombinant soluble Hu-B1.219 protein. Methods for expression and purification of Hu-B1.219 are described in Section 5.2, supra, and may be used to express recombinant full length Hu-B1.219 or fragments of Hu-B1.219 depending on the functional domains of interest. For example, the cytoplasmic and extracellular ligand binding domains of Hu-B1.219 may be separately expressed and used to screen peptide libraries.

To identify and isolate the peptide/solid phase support that interacts and forms a complex with Hu-B1.219, it is necessary to label or "tag" the Hu-B1.219 molecule. The Hu-B1.219 protein may be conjugated to enzymes such as alkaline phosphatase or horseradish peroxidase or to other reagents such as fluorescent labels which may include fluorescein isothiocyanate (FITC), phycoerythrin (PE) or rhodamine. Conjugation of any given label to Hu-B1.219 may be performed using techniques that are routine in the art. Alternatively, Hu-B1.219 expression vectors may be engineered to express a chimeric Hu-B1.219 protein containing an epitope for which a commercially available antibody exist. The epitope specific antibody may be tagged using methods well known in the art including labeling with enzymes, fluorescent dyes or colored or magnetic beads.

The "tagged" Hu-B1.219 conjugate is incubated with the random peptide library for 30 minutes to one hour at 22° C. to allow complex formation between Hu-B1.219 and peptide species within the library. The library is then washed to remove any unbound Hu-B1.219 protein. If Hu-B1.219 has been conjugated to alkaline phosphatase or horseradish peroxidase the whole library is poured into a petri dish containing substrates for either alkaline phosphatase or peroxidase, for example, 5-bromo-4-chloro-3-indoyl phosphate (BCIP) or 3,3',4,"-diaminobenzidine (DAB), respectively. After incubating for several minutes, the peptide/solid phase-Hu-B1.219 complex changes color, and can be easily identified and isolated physically under a dissecting microscope with a micromanipulator. If a fluorescent tagged Hu-B1.219 molecule has been used, complexes may be isolated by fluorescent activated sorting. If a chimeric Hu-B1.219 protein expressing a heterologous epitope has been used, detection of the peptide/Hu-B1.219 complex may be accomplished by using a labeled epitope specific antibody. Once isolated, the identity of the peptide attached to the solid phase support may be determined by peptide sequencing.

In addition to using soluble Hu-B1.219 molecules, in another embodiment, it is possible to detect peptides that bind to cell surface receptors using intact cells. The use of intact cells is preferred for use with receptors that are multi-subunits or labile or with receptors that require the lipid domain of the cell membrane to be functional. Methods for generating cell lines expressing Hu-B1.219 are described in Section 5.3. The cells used in this technique may be either live or fixed cells. The cells may be incubated with the random peptide library and bind to certain peptides in the library to form a "rosette" between the target cells and the relevant solid phase support/peptide. The rosette can thereafter be isolated by differential centrifugation or removed physically under a dissecting microscope.

As an alternative to whole cell assays for membrane bound receptors or receptors that require the lipid domain of the cell membrane to be functional, the receptor molecules can be reconstituted into liposomes where label or "tag" can be attached.

Various procedures known in the art may be used for the production of antibodies to epitopes of the recombinantly produced Hu-B1.219 receptor. Such antibodies include but are not limited to polyclonal, monoclonal, chimeric, single chain, Fab fragments and fragments produced by an Fab expression library. Neutralizing antibodies i.e., those which compete for the ligand binding site of the receptor are especially preferred for diagnostics and therapeutics.

Monoclonal antibodies that bind Hu-B1.219 may be radioactively labeled allowing one to follow their location and distribution in the body after injection. Radioisotope tagged antibodies may be used as a non-invasive diagnostic tool for imaging de novo cells of tumors and metastases.

Immunotoxins may also be designed which target cytotoxic agents to specific sites in the body. For example, high affinity Hu-B1.219 specific monoclonal antibodies may be covalently complexed to bacterial or plant toxins, such as diphtheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate Hu-B1.219 expressing tumor cells.

For the production of antibodies, various host animals may be immunized by injection with the Hu-B1.219 protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to Hu-B1.219 may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce Hu-B1.219-specific single chain antibodies.

Antibody fragments which contain specific binding sites of Hu-B1.219 may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to Hu-B1.219.

5.6 USES OF Hu-B1.219 POLYNUCLEOTIDE

An Hu-B1.219 polynucleotide may be used for diagnostic and/or therapeutic purposes. For diagnostic purposes, an Hu-B1.219 polynucleotide may be used to detect Hu-B1.219 gene expression or aberrant Hu-B1.219 gene expression in disease states, e.g., chronic myelogenous leukemia. Included in the scope of the invention are oligonucleotide sequences, that include antisense RNA and DNA molecules and ribozymes, that function to inhibit translation of an Hu-B1.219.

5.6.1. DIAGNOSTIC USES OF AN Hu-B1.219 POLYNUCLEOTIDE

An Hu-B1.219 polynucleotide may have a number of uses for the diagnosis of diseases resulting from aberrant expression of Hu-B1.219. For example, the Hu-B1.219 DNA sequence may be used in hybridization assays of biopsies or autopsies to diagnose abnormalities of Hu-B1.219 expression; e.g., Southern or Northern analysis, including in situ hybridization assays. Such techniques are well known in the art, and are in fact the basis of many commercially available diagnostic kits.

5.6.2. THERAPEUTIC USES OF AN Hu-B1.219 POLYNUCLEOTIDE

An Hu-B1.219 polynucleotide may be useful in the treatment of various abnormal conditions. By introducing gene sequences into cells, gene therapy can be used to treat conditions in which the cells do not proliferate or differentiate normally due to underexpression of normal Hu-B1.219 or expression of abnormal/inactive Hu-B1.219. In some instances, the polynucleotide encoding an Hu-B1.219 is intended to replace or act in the place of a functionally deficient endogenous gene. Alternatively, abnormal conditions characterized by overproliferation can be treated using the gene therapy techniques described below.

Abnormal cellular proliferation is an important component of a variety of disease states. Recombinant gene therapy vectors, such as viral vectors, may be engineered to express variant, signalling incompetent forms of Hu-B1.219 which may be used to inhibit the activity of the naturally occurring endogenous Hu-B1.219. A signalling incompetent form may be, for example, a truncated form of the protein that is lacking all or part of its signal transduction domain. Such a truncated form may participate in normal binding to a substrate but lack signal transduction activity. Thus recombinant gene therapy vectors may be used therapeutically for treatment of diseases resulting from aberrant expression or activity of an Hu-B1.219. Accordingly, the invention provides a method of inhibiting the effects of signal transduction by an endogenous Hu-B1.219 protein in a cell comprising delivering a DNA molecule encoding a signalling incompetent form of the Hu-B1.219 protein to the cell so that the signalling incompetent Hu-B1.219 protein is produced in the cell and competes with the endogenous Hu-B1.219 protein for access to molecules in the Hu-B1.219 protein signalling pathway which activate or are activated by the endogenous Hu-B1.219 protein.

Expression vectors derived from viruses such as retroviruses, vaccinia virus, adeno-associated virus, herpes viruses, or bovine papilloma virus, may be used for delivery of recombinant Hu-B1.219 into the targeted cell population. Methods which are well known to those skilled in the art can be used to construct recombinant viral vectors containing an Hu-B1.219 polynucleotide sequence. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant Hu-B1.219 molecules can be reconstituted into liposomes for delivery to target cells.

Oligonucleotide sequences, that include anti-sense RNA and DNA molecules and ribozymes that function to inhibit the translation of an Hu-B1.219 mRNA are within the scope of the invention. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of an Hu-B1.219 nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of Hu-B1.219 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

Methods for introducing polynucleotides into such cells or tissue include methods for in vitro introduction of polynucleotides such as the insertion of naked polynucleotide, i.e., by injection into tissue, the introduction of an Hu-B1.219 polynucleotide in a cell ex vivo, i.e., for use in autologous cell therapy, the use of a vector such as a virus, retrovirus, phage or plasmid, etc. or techniques such as electroporation which may be used in vivo or ex vivo.

6. EXAMPLE: MOLECULAR CLONING OF A NOVEL HEMATOPOIETIN RECEPTOR COMPLEMENTARY DNA

6.1 MATERIALS AND METHODS

6.1.1 NORTHERN BLOT ANALYSIS

In order to study the expression of the Hu-B1.219 gene, Northern blots containing RNA obtained from a variety of human tissues (Clontech, Palo Alto, Calif.) was probed with a radiolabeled 530 bp DNA probe corresponding to nucleotides 143 through 672 (see FIGS. 2A–2D). Briefly, the blots were prehybridized at 42° C. for 3–6 hours in a solution containing 5×SSPE, 10×Denhardt's solution, 100 ug/ml freshly denatured, sheared salmon sperm DNA, 50% formamide (freshly deionized), and 2% SDS. The radiolabeled probe was heat denatured and added to the prehybridization mix and allowed to hybridize at 42° C. for 18–24 hours with constant shaking. The blots were rinsed in 2×SSC, 0.05% SDS several times at room temperature before being transferred to a wash solution containing 0.1×SSC, 0.1% SDS and agitated at 50° C. for 40 minutes. The blots were then covered with plastic wrap, mounted on Whatman paper and exposed to x-ray film at −70° C. using an intensifying screen.

6.2 RESULTS

A number of cDNA clones were isolated from a human fetal liver cDNA library (Clontech, Palo Alto, Calif.), and DNA sequences from several clones were determined. Several of these clones (Hu-B1.219 #4, #33, #34) contained overlapping sequences, which were then compiled into a contiguous nucleotide sequence. Both the cDNA and predicted protein sequence from this cDNA fragment are shown in FIGS. 2A–2D. This partial cDNA clone contains two FN III domains including the presence of "WS box", which are characteristic of genes of the HR family. Thus, this cDNA fragment represents a novel member of the HR gene family, herein referred to as Hu-B1.219 (Table 1).

Various human tissue RNA was probed with a radiolabelled Hu-B1.219 fragment corresponding to nucleotide numbers from 143 to 672 as disclosed in FIGS. 2A–2D for Northern blot analyses. Two different size mRNAs were detected. This result suggests that there may be another homologous gene or there is alternative splicing of a single RNA transcript. Hu-B1.219 expression was by far the strongest in human fetal tissues, particularly the liver and lung. Trace levels were found in several adult tissues. Interestingly, a chronic myelogenous leukemia cell line, K562, was strongly positive for its expression, while some expression was also detected in A549 cells, a lung carcinoma cell line (Table 2).

Taken together, the data indicates that the Hu-B1.219 cDNA clone represents a new member of the hematopoietin receptor family. A summary of the data that supports this conclusion is as follows:

1. The Hu-B1.219 DNA and protein sequences do not fully match any known sequences in the corresponding computer data bases.
2. Hu-B1.219 shares certain DNA sequence homology with the IL-6R and IL-4R.
3. It shares certain protein homology with G-CSFR, IL-6R, IL-3R beta chain, gp130, IL-12R, and LIFR.
4. It contains two "WS box" motifs with the correct spacing of conserved amino acids in both FN III domains (see FIG. 3).
5. It contains an amphipathic sequence in block 3 of both FN III domains (see FIG. 4).
6. It contains alternating hydrophobic and basic amino acids in block 6 of both FN III domains (see FIG. 5).
7. It contains conserved cysteines in these cysteine rich regions upstream of both FN III domains.
8. It was originally cloned from a hematopoietic tissue, fetal liver.
9. It is expressed by certain fetal tissues.

7. Deposit of Microorganisms

The following organisms were deposited with the American Type Culture Collection (ATCC), 12301 Parklawn Drive, Rockville, Md. 20852.
Strain Designation Accession No.
HUB1.219, #1
HUB1.219, #4
HUB1.219, #8
HUB1.219, #33
HUB1.219, #34
HUB1.219, #36

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

TABLE 1

Cytokine Receptor Gene FN III Domain Sizes (bp)

| Gene | Human | Mouse | Rat |
| --- | --- | --- | --- |
| Hu-B1.219(5') | 273 | | |
| Hu-B1.219(3') | 282 | | |
| IL-2Rβ | 291 | 288 | 291 |
| IL-2Rγ | 273 | | |
| IL-3Rα | 246 | 252 | |
| IL-3RβAic2a | | 306 and 273 | |
| IL-3RβAic2b | 306 and 282 | 303 and 276 | |
| IL-4R | 294 | | 291 |
| IL-5Rα | 276 | 273 | |
| IL-6R | 288 | 285 | |
| gp130 | 288 | 291 | 288 |
| IL-7R | | 294 | |
| IL-9R | 321 | 321 | |
| mpl | | 270 | |
| G-CSFR | 300 | 297 | |
| GM-CSFR | 288 | | |
| CNTFR | 282 | | 285 |
| PRLR | | | 288 |
| EPOR | 288 | 285 | 288 |
| LIFR-1 | 321 and 297 | | |

TABLE 2

SUMMARY OF NORTHERN BLOT ANALYSIS OF Hu-B1.219 GENE EXPRESSION

| | Tissue/cell line | Expression |
| --- | --- | --- |
| HUMAN: | fetal brain | − |
| | lung | +++ |
| | liver | +++++ |
| | kidney | + |
| | adult heart | + |
| | brain | − |
| | placenta | +/− |
| | lung | + |
| | liver | + |
| | skeletal muscle | − |
| | kidney | +/− |
| | pancreas | − |
| | spleen | − |
| | thymus | − |
| | prostate | − |
| | testis | − |
| | ovary | + |
| | small intestine | − |
| | colon | − |
| | peripheral blood leukocytes | − |
| cancer | HL-60 | − |
| | HeLa | − |
| | K-562 | +++ |
| | MOLT-4 | − |
| | Raji | − |
| | SW480 | − |
| | A549 | + |
| | G361 | − |

What is claimed is:

1. An isolated nucleic acid molecule, comprising a nucleotide sequence that hybridizes under stringent conditions to a second nucleic acid molecule having the nucleotide sequence of SEQ ID NO: 2 between resides #143 and #672, or its complement.

2. An isolated nucleic acid molecule, comprising a nucleotide sequence that hybridizes under stringent conditions to a second nucleic acid molecule having the nucleotide sequence of SEQ ID NO: 2, or its complement.

3. An isolated nucleic acid molecule, comprising a nucleotide sequence that (a) encodes a polypeptide having the amino acid sequence of SEQ ID NO: 3, or (b) is the complement of the nucleotide sequence.

4. The nucleic acid molecule of claim 1, 2 or 3 which is a cDNA.

5. The nucleic acid molecule of claim 1, 2 or 3 which is a genomic DNA.

6. The nucleic acid molecule of claim 1, 2 or 3 which is a double helix.

7. A recombinant vector containing the nucleic acid molecule of claim 1, 2 or 3.

8. An expression vector containing the nucleic acid molecule of claim 1, 2 or 3 in which the nucleotide sequence is operatively associated with a regulatory nucleotide sequence that controls expression of the nucleotide sequence in a host cell.

9. A genetically-engineered host cell containing the nucleic acid molecule of claim 1, 2 or 3.

10. A genetically-engineered host cell containing the nucleic acid molecule of claim 1, 2 or 3 in which the nucleotide sequence is operatively associated with a regulatory sequence that controls expression of the nucleotide sequence in the host cell.

11. The genetically-engineered host cell of claim 10 in which the host cell is a prokaryote.

12. The genetically-engineered host cell of claim 10 in which the host cell is an eukaryote.

13. A method for producing a polypeptide, comprising:

(a) culturing the genetically-engineered host cell of claim 11; and (b) recovering the polypeptide from the cultured host cell or its culture medium.

14. A method for producing a polypeptide, comprising:

(a) culturing the genetically-engineered host cell of claim 12; and (b) recovering the polypeptide from the cultured host cell or its culture medium.

* * * * *

UNITED STATES PATENT AND TRADEMARK OFFICE
CERTIFICATE OF CORRECTION

PATENT NO. : 5,643,748
DATED : July 1, 1997
INVENTOR(S) : Snodgrass *et al.*

It is certified that error appears in the above-identified patent and that said Letters Patent is hereby corrected as shown below:

At column 5, line 50, change "Crea and Horn, 180" to --Crea and Horn, 1980--.

At column 10, line 26, after "Alternatively," delete "be".

Signed and Sealed this

Seventeenth Day of October, 2000

Attest:

Q. TODD DICKINSON

*Attesting Officer*      *Director of Patents and Trademarks*

UNITED STATES PATENT AND TRADEMARK OFFICE
CERTIFICATE OF CORRECTION

PATENT NO. : 5,643,748  
APPLICATION NO. : 08/306231  
DATED : July 1, 1997  
INVENTOR(S) : Snodgrass et al.

Page 1 of 1

It is certified that error appears in the above-identified patent and that said Letters Patent is hereby corrected as shown below:

At line 4 of claim 1 (column 29, line 21), please replace "resides" with -- residues --.

Signed and Sealed this

Tenth Day of July, 2007

JON W. DUDAS  
*Director of the United States Patent and Trademark Office*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:1:

Trp  Ser  Xaa  Trp  Ser
    1                           5

( 2 ) INFORMATION FOR SEQ ID NO:2:

( i ) SEQUENCE CHARACTERISTICS:
        ( A ) LENGTH: 1707 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 1..1707

( x i ) SEQUENCE DESCRIPTION: SEQ ID NO:2:

```
ACA GTA AAT TCT TTA GTT TTT CAA CCA ATA GAT GCA AAC TGG AAC ATA         48
Thr Val Asn Ser Leu Val Phe Gln Pro Ile Asp Ala Asn Trp Asn Ile
 1               5                  10                  15

CAG TGC TGG CTA AAA GGA GAC TTA AAA TTA TTC ATC TGT TAT GTG GAG         96
Gln Cys Trp Leu Lys Gly Asp Leu Lys Leu Phe Ile Cys Tyr Val Glu
             20                  25                  30

TCA TTA TTT AAG AAT CTA GTC AAG AAT TAT AAC TAT AAG GTC CAT CTT        144
Ser Leu Phe Lys Asn Leu Val Lys Asn Tyr Asn Tyr Lys Val His Leu
         35                  40                  45

TTA TAT GTT CTG CCT GAA GTG TTA GAA GAT TCA CCT CTG GTT CCC CAA        192
Leu Tyr Val Leu Pro Glu Val Leu Glu Asp Ser Pro Leu Val Pro Gln
     50                  55                  60

AAA GGC AGT TTT CAG ATG GTT CAC TGC AAT TGC AGT GTT CAT GAA TGT        240
Lys Gly Ser Phe Gln Met Val His Cys Asn Cys Ser Val His Glu Cys
 65                  70                  75                  80

TGT GAA TGT CTT GTG CCT GTG CCA ACA GCC AAA CTC AAC GAC ACT CTC        288
Cys Glu Cys Leu Val Pro Val Pro Thr Ala Lys Leu Asn Asp Thr Leu
                 85                  90                  95

CTT ATG TGT TTG AAA ATC ACA TCT GGT GGA GTA ATT TTC CGG TCA CCT        336
Leu Met Cys Leu Lys Ile Thr Ser Gly Gly Val Ile Phe Arg Ser Pro
            100                 105                 110

CTA ATG TCA GTT CAG CCC ATA AAT ATG GTG AAG CCT GAT CCA CCA TTA        384
Leu Met Ser Val Gln Pro Ile Asn Met Val Lys Pro Asp Pro Pro Leu
        115                 120                 125

GGT TTG CAT ATG GAA ATC ACA GAT GAT GGT AAT TTA AAG ATT TCT TGG        432
Gly Leu His Met Glu Ile Thr Asp Asp Gly Asn Leu Lys Ile Ser Trp
    130                 135                 140

TCC AGC CCA CCA TTG GTA CCA TTT CCA CTT CAA TAT CAA GTG AAA TAT        480
Ser Ser Pro Pro Leu Val Pro Phe Pro Leu Gln Tyr Gln Val Lys Tyr
145                 150                 155                 160
```

```
TCA GAG AAT TCT ACA ACA GTT ATC AGA GAA GCT GAC AAG ATT GTC TCA         528
Ser Glu Asn Ser Thr Thr Val Ile Arg Glu Ala Asp Lys Ile Val Ser
                165             170             175

GCT ACA TCC CTG CTA GTA GAC AGT ATA CTT CCT GGG TCT TCG TAT GAG         576
Ala Thr Ser Leu Leu Val Asp Ser Ile Leu Pro Gly Ser Ser Tyr Glu
                180             185             190

GTT CAG GTG AGG GGC AAG AGA CTG GAT GGC CCA GGA ATC TGG AGT GAC         624
Val Gln Val Arg Gly Lys Arg Leu Asp Gly Pro Gly Ile Trp Ser Asp
                195             200             205

TGG AGT ACT CCT CGT GTC TTT ACC ACA CAA GAT GTC ATA TAC TTT CCA         672
Trp Ser Thr Pro Arg Val Phe Thr Thr Gln Asp Val Ile Tyr Phe Pro
        210             215             220

CCT AAA ATT CTG ACA AGT GTT GGG TCT AAT GTT TCT TTT CAC TGC ATC         720
Pro Lys Ile Leu Thr Ser Val Gly Ser Asn Val Ser Phe His Cys Ile
225             230             235             240

TAT AAG AAG GAA AAC AAG ATT GTT CCC TCA AAA GAG ATT GTT TGG TGG         768
Tyr Lys Lys Glu Asn Lys Ile Val Pro Ser Lys Glu Ile Val Trp Trp
                245             250             255

ATG AAT TTA GCT GAG AAA ATT CCT CAA AGC CAG TAT GAT GTT GTG AGT         816
Met Asn Leu Ala Glu Lys Ile Pro Gln Ser Gln Tyr Asp Val Val Ser
                260             265             270

GAT CAT GTT AGC AAA GTT ACT TTT TTC AAT CTG AAT GAA ACC AAA CCT         864
Asp His Val Ser Lys Val Thr Phe Phe Asn Leu Asn Glu Thr Lys Pro
                275             280             285

CGA GGA AAG TTT ACC TAT GAT GCA GTG TAC TGC TGC AAT GAA CAT GAA         912
Arg Gly Lys Phe Thr Tyr Asp Ala Val Tyr Cys Cys Asn Glu His Glu
                290             295             300

TGC CAT CAT CGC TAT GCT GAA TTA TAT GTG ATT GAT GTC AAT ATC AAT         960
Cys His His Arg Tyr Ala Glu Leu Tyr Val Ile Asp Val Asn Ile Asn
305             310             315             320

ATC TCA TGT GAA ACT GAT GGG TAC TTA ACT AAA ATG ACT TGC AGA TGG        1008
Ile Ser Cys Glu Thr Asp Gly Tyr Leu Thr Lys Met Thr Cys Arg Trp
                325             330             335

TCA ACC AGT ACA ATC CAG TCA CTT GCG GAA AGC ACT TTG CAA TTG AGG        1056
Ser Thr Ser Thr Ile Gln Ser Leu Ala Glu Ser Thr Leu Gln Leu Arg
            340             345             350

TAT CAT AGG AGC AGC CTT TAC TGT TCT GAT ATT CCA TCT ATT CAT CCC        1104
Tyr His Arg Ser Ser Leu Tyr Cys Ser Asp Ile Pro Ser Ile His Pro
            355             360             365

ATA TCT GAG CCC AAA GAT TGC TAT TTG CAG AGT GAT GGT TTT TAT GAA        1152
Ile Ser Glu Pro Lys Asp Cys Tyr Leu Gln Ser Asp Gly Phe Tyr Glu
    370             375             380

TGC ATT TTC CAG CCA ATC TTC CTA TTA TCT GGC TAC ACA ATG TGG ATT        1200
Cys Ile Phe Gln Pro Ile Phe Leu Leu Ser Gly Tyr Thr Met Trp Ile
385             390             395             400

AGG ATC AAT CAC TCT CTA GGT TCA CTT GAC TCT CCA CCA ACA TGT GTC        1248
Arg Ile Asn His Ser Leu Gly Ser Leu Asp Ser Pro Pro Thr Cys Val
                405             410             415

CTT CCT GAT TCT GTG GTG AAG CCA CTG CCT CCA TCC AGT GTG AAA GCA        1296
Leu Pro Asp Ser Val Val Lys Pro Leu Pro Pro Ser Ser Val Lys Ala
            420             425             430

GAA ATT ACT ATA AAC ATT GGA TTA TTG AAA ATA TCT TGG GAA AAG CCA        1344
Glu Ile Thr Ile Asn Ile Gly Leu Leu Lys Ile Ser Trp Glu Lys Pro
            435             440             445

GTC TTT CCA GAG AAT AAC CTT CAA TTC CAG ATT CGC TAT GGT TTA AGT        1392
Val Phe Pro Glu Asn Asn Leu Gln Phe Gln Ile Arg Tyr Gly Leu Ser
    450             455             460

GGA AAA GAA GTA CAA TGG AAG ATG TAT GAG GTT TAT GAT GCA AAA TCA        1440
Gly Lys Glu Val Gln Trp Lys Met Tyr Glu Val Tyr Asp Ala Lys Ser
465             470             475             480
```

| AAA | TCT | GTC | AGT | CTC | CCA | GTT | CCA | GAC | TTG | TGT | GCA | GTC | TAT | GCT | GTT | 1488 |
| Lys | Ser | Val | Ser | Leu | Pro | Val | Pro | Asp | Leu | Cys | Ala | Val | Tyr | Ala | Val | |
| | | | | 485 | | | | 490 | | | | | | 495 | | |
| CAG | GTG | CGC | TGT | AAG | AGG | CTA | GAT | GGA | CTG | GGA | TAT | TGG | AGT | AAT | TGG | 1536 |
| Gln | Val | Arg | Cys | Lys | Arg | Leu | Asp | Gly | Leu | Gly | Tyr | Trp | Ser | Asn | Trp | |
| | | | 500 | | | | 505 | | | | | 510 | | | | |
| AGC | AAT | CCA | GCC | TAC | ACA | GTT | GTC | ATG | GAT | ATA | AAA | GTT | CCT | ATG | AGA | 1584 |
| Ser | Asn | Pro | Ala | Tyr | Thr | Val | Val | Met | Asp | Ile | Lys | Val | Pro | Met | Arg | |
| | | 515 | | | | | 520 | | | | | 525 | | | | |
| GGA | CCT | GAA | TTT | TGG | AGA | ATA | ATT | AAT | GGA | GAT | ACT | ATG | AAA | AAG | GAG | 1632 |
| Gly | Pro | Glu | Phe | Trp | Arg | Ile | Ile | Asn | Gly | Asp | Thr | Met | Lys | Lys | Glu | |
| | 530 | | | | | 535 | | | | | 540 | | | | | |
| AAA | AAT | GTC | ACT | TTA | CTT | TGG | AAG | CCC | CTG | ATG | AAA | AAT | GAC | TCA | TTG | 1680 |
| Lys | Asn | Val | Thr | Leu | Leu | Trp | Lys | Pro | Leu | Met | Lys | Asn | Asp | Ser | Leu | |
| 545 | | | | | 550 | | | | | 555 | | | | | 560 | |
| TGC | AGT | GTT | CAG | AGA | TAT | GTG | ATA | AAC | | | | | | | | 1707 |
| Cys | Ser | Val | Gln | Arg | Tyr | Val | Ile | Asn | | | | | | | | |
| | | | | 565 | | | | | | | | | | | | |

( 2 ) INFORMATION FOR SEQ ID NO:3:

( i ) SEQUENCE CHARACTERISTICS:
( A ) LENGTH: 569 amino acids
( B ) TYPE: amino acid
( D ) TOPOLOGY: linear ( i i ) MOLECULE TYPE: protein ( x i ) SEQUENCE DESCRIPTION: SEQ ID NO:3:

| Thr | Val | Asn | Ser | Leu | Val | Phe | Gln | Pro | Ile | Asp | Ala | Asn | Trp | Asn | Ile |
| 1 | | | | 5 | | | | | 10 | | | | | | 15 |
| Gln | Cys | Trp | Leu | Lys | Gly | Asp | Leu | Lys | Leu | Phe | Ile | Cys | Tyr | Val | Glu |
| | | | 20 | | | | | 25 | | | | | 30 | | |
| Ser | Leu | Phe | Lys | Asn | Leu | Val | Lys | Asn | Tyr | Asn | Tyr | Lys | Val | His | Leu |
| | | 35 | | | | | 40 | | | | | 45 | | | |
| Leu | Tyr | Val | Leu | Pro | Glu | Val | Leu | Glu | Asp | Ser | Pro | Leu | Val | Pro | Gln |
| | 50 | | | | | 55 | | | | | 60 | | | | |
| Lys | Gly | Ser | Phe | Gln | Met | Val | His | Cys | Asn | Cys | Ser | Val | His | Glu | Cys |
| 65 | | | | | 70 | | | | 75 | | | | | | 80 |
| Cys | Glu | Cys | Leu | Val | Pro | Val | Pro | Thr | Ala | Lys | Leu | Asn | Asp | Thr | Leu |
| | | | | 85 | | | | | 90 | | | | | 95 | |
| Leu | Met | Cys | Leu | Lys | Ile | Thr | Ser | Gly | Val | Ile | Phe | Arg | Ser | Pro | |
| | | | | 100 | | | | | 105 | | | | | 110 | |
| Leu | Met | Ser | Val | Gln | Pro | Ile | Asn | Met | Val | Lys | Pro | Asp | Pro | Pro | Leu |
| | | | 115 | | | | 120 | | | | | 125 | | | |
| Gly | Leu | His | Met | Glu | Ile | Thr | Asp | Asp | Gly | Asn | Leu | Lys | Ile | Ser | Trp |
| | 130 | | | | | 135 | | | | | 140 | | | | |
| Ser | Ser | Pro | Pro | Leu | Val | Pro | Phe | Pro | Leu | Gln | Tyr | Gln | Val | Lys | Tyr |
| 145 | | | | | 150 | | | | | 155 | | | | | 160 |
| Ser | Glu | Asn | Ser | Thr | Thr | Val | Ile | Arg | Glu | Ala | Asp | Lys | Ile | Val | Ser |
| | | | | 165 | | | | | 170 | | | | | 175 | |
| Ala | Thr | Ser | Leu | Leu | Val | Asp | Ser | Ile | Leu | Pro | Gly | Ser | Ser | Tyr | Glu |
| | | | 180 | | | | | 185 | | | | 190 | | | |
| Val | Gln | Val | Arg | Gly | Lys | Arg | Leu | Asp | Gly | Pro | Gly | Ile | Trp | Ser | Asp |
| | | | 195 | | | | | 200 | | | | | 205 | | |
| Trp | Ser | Thr | Pro | Arg | Val | Phe | Thr | Thr | Gln | Asp | Val | Ile | Tyr | Phe | Pro |
| | 210 | | | | | 215 | | | | | 220 | | | | |
| Pro | Lys | Ile | Leu | Thr | Ser | Val | Gly | Ser | Asn | Val | Ser | Phe | His | Cys | Ile |
| 225 | | | | | 230 | | | | | 235 | | | | | 240 |

```
Tyr  Lys  Lys  Glu  Asn  Lys  Ile  Val  Pro  Ser  Lys  Glu  Ile  Val  Trp  Trp
               245                      250                      255

Met  Asn  Leu  Ala  Glu  Lys  Ile  Pro  Gln  Ser  Gln  Tyr  Asp  Val  Val  Ser
               260                      265                      270

Asp  His  Val  Ser  Lys  Val  Thr  Phe  Phe  Asn  Leu  Asn  Glu  Thr  Lys  Pro
               275                      280                      285

Arg  Gly  Lys  Phe  Thr  Tyr  Asp  Ala  Val  Tyr  Cys  Cys  Asn  Glu  His  Glu
          290                      295                      300

Cys  His  His  Arg  Tyr  Ala  Glu  Leu  Tyr  Val  Ile  Asp  Val  Asn  Ile  Asn
305                           310                      315                      320

Ile  Ser  Cys  Glu  Thr  Asp  Gly  Tyr  Leu  Thr  Lys  Met  Thr  Cys  Arg  Trp
                    325                      330                      335

Ser  Thr  Ser  Thr  Ile  Gln  Ser  Leu  Ala  Glu  Ser  Thr  Leu  Gln  Leu  Arg
               340                      345                      350

Tyr  His  Arg  Ser  Ser  Leu  Tyr  Cys  Ser  Asp  Ile  Pro  Ser  Ile  His  Pro
               355                      360                      365

Ile  Ser  Glu  Pro  Lys  Asp  Cys  Tyr  Leu  Gln  Ser  Asp  Gly  Phe  Tyr  Glu
          370                      375                      380

Cys  Ile  Phe  Gln  Pro  Ile  Phe  Leu  Leu  Ser  Gly  Tyr  Thr  Met  Trp  Ile
385                           390                      395                      400

Arg  Ile  Asn  His  Ser  Leu  Gly  Ser  Leu  Asp  Ser  Pro  Pro  Thr  Cys  Val
                    405                      410                      415

Leu  Pro  Asp  Ser  Val  Val  Lys  Pro  Leu  Pro  Pro  Ser  Ser  Val  Lys  Ala
               420                      425                      430

Glu  Ile  Thr  Ile  Asn  Ile  Gly  Leu  Leu  Lys  Ile  Ser  Trp  Glu  Lys  Pro
               435                      440                      445

Val  Phe  Pro  Glu  Asn  Asn  Leu  Gln  Phe  Gln  Ile  Arg  Tyr  Gly  Leu  Ser
     450                      455                      460

Gly  Lys  Glu  Val  Gln  Trp  Lys  Met  Tyr  Glu  Val  Tyr  Asp  Ala  Lys  Ser
465                           470                      475                      480

Lys  Ser  Val  Ser  Leu  Pro  Val  Pro  Asp  Leu  Cys  Ala  Val  Tyr  Ala  Val
               485                      490                      495

Gln  Val  Arg  Cys  Lys  Arg  Leu  Asp  Gly  Leu  Gly  Tyr  Trp  Ser  Asn  Trp
          500                      505                      510

Ser  Asn  Pro  Ala  Tyr  Thr  Val  Val  Met  Asp  Ile  Lys  Val  Pro  Met  Arg
          515                      520                      525

Gly  Pro  Glu  Phe  Trp  Arg  Ile  Ile  Asn  Gly  Asp  Thr  Met  Lys  Lys  Glu
          530                      535                      540

Lys  Asn  Val  Thr  Leu  Leu  Trp  Lys  Pro  Leu  Met  Lys  Asn  Asp  Ser  Leu
545                           550                      555                      560

Cys  Ser  Val  Gln  Arg  Tyr  Val  Ile  Asn
                    565
```

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:4:

```
Glu  Pro  Tyr  Leu  Glu  Phe  Glu  Ala  Arg  Arg  Arg  Leu  Leu
 1             5                        10
```

(2) INFORMATION FOR SEQ ID NO:5:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:5:

```
Glu His Leu Val Gln Tyr Arg Thr Asp Trp Asp His Ser
 1               5                  10
```

(2) INFORMATION FOR SEQ ID NO:6:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:6:

```
Asp His Cys Phe Asn Tyr Glu Leu Lys Ile Tyr Asn Thr
 1               5                  10
```

(2) INFORMATION FOR SEQ ID NO:7:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:7:

```
Thr Thr His Ile Arg Tyr Glu Val Asp Val Ser Ala Gly
 1               5                  10
```

(2) INFORMATION FOR SEQ ID NO:8:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:8:

```
Pro Phe Pro Leu Gln Tyr Gln Val Lys Tyr Gln Val Lys
 1               5                  10
```

(2) INFORMATION FOR SEQ ID NO:9:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:9:

```
Gln Phe Gln Ile Arg Tyr Gly Leu Ser Gly Lys Glu Val
 1               5                  10
```

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:10:

```
Ser  Thr  Ser  Tyr  Glu  Val  Gln  Val  Arg  Val  Lys  Ala  Gln  Arg  Asn
1                  5                        10                       15
```

( 2 ) INFORMATION FOR SEQ ID NO:11:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:11:

```
Gln  Lys  Arg  Tyr  Thr  Phe  Arg  Val  Arg  Ser  Arg  Phe  Asn  Pro  Leu
1                  5                        10                       15
```

( 2 ) INFORMATION FOR SEQ ID NO:12:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:12:

```
Leu  Ser  Lys  Tyr  Asp  Val  Gln  Val  Arg  Ala  Ala  Val  Ser  Ser  Met
1                  5                        10                       15
```

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:13:

```
Gly  Thr  Arg  Tyr  Thr  Phe  Ala  Val  Arg  Ala  Arg  Met  Ala  Pro  Ser
1                  5                        10                       15
```

( 2 ) INFORMATION FOR SEQ ID NO:14:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:14:

```
Gly  Ser  Ser  Tyr  Glu  Val  Gln  Val  Arg  Gly  Lys  Arg  Leu  Asp  Gly
1                  5                        10                       15
```

( 2 ) INFORMATION FOR SEQ ID NO:15:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:15:

```
Cys Ala Val Tyr Ala Val Gln Val Arg Cys Lys Arg Leu Asp Gly
 1           5                   10                      15
```